United States Patent [19]

Georgiev et al.

[11] Patent Number: 4,625,040
[45] Date of Patent: Nov. 25, 1986

[54] N-(PHENYL) OR N-(PHENYLCYCLOPROPYL)-2,5-DIHYDRO-2-OXO-4[(SUBSTITUTED PHENYL)AMINO]-3-FURANCARBOXAMIDE DERIVATIVES

[75] Inventors: Vassil S. Georgiev; Robert A. Mack, both of Rochester, N.Y.

[73] Assignee: Pennwalt Corporation, Philadelphia, Pa.

[21] Appl. No.: 839,298

[22] Filed: Mar. 13, 1986

Related U.S. Application Data

[63] Continuation-in-part of Ser. No. 653,254, Sep. 24, 1984.

[51] Int. Cl.$^4$ .......................................... C07D 307/68
[52] U.S. Cl. .................................................... 549/321
[58] Field of Search ........................................ 549/321

[56] References Cited

PUBLICATIONS

M. Sone et al, Chem. Pharm. Bull., vol. 22(3) (1974), pp. 617–622.

*Primary Examiner*—Norma S. Milestone

[57] ABSTRACT

Compounds which possess antiallergy activity have the formula:

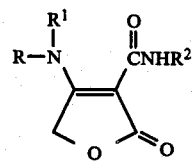

wherein R is selected from phenyl and phenyl mono or disubstituted with lower alkyl, nitro, halogenated methyl, halogen, lower alkoxy and combinations thereof;

wherein $R^1$ is selected from hydrogen and lower alkyl; and where $R^2$ is selected from phenyl, phenyl monosubstituted with lower alkyl, nitro, halogenated methyl, halogen, and lower alkoxy, and trans-phenylcyclopropyl in which the phenyl group may be substituted with lower alkyl or halogen.

12 Claims, No Drawings

N-(PHENYL) OR N-(PHENYLCYCLOPROPYL)-2,5-DIHYDRO-2-OXO-4[(SUBSTITUTED PHENYL)AMINO]-3-FURANCARBOXAMIDE DERIVATIVES

This application is a continuation-in-part of application Ser. No. 653,254, filed Sept. 24, 1984.

BACKGROUND OF THE INVENTION

This invention relates generally to lactone derivatives of 2,5-dihydrofurans and more specifically to N-(phenyl) or N-(phenylcyclopropyl)-2,5-dihydro-2-oxo-4[(substituted phenyl)amino]-3-furancarboxamides which have antiallergy properties.

BRIEF SUMMARY OF THE INVENTION

In accordance with this invention there are provided compounds of the formula:

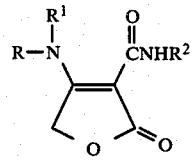

where R is selected from phenyl and phenyl mono or disubstituted with lower alkyl, nitro, halogenated methyl, halogen, lower alkoxy and combinations thereof;

Where $R^1$ is selected from hydrogen and lower alkyl; and

Where $R^2$ is selected from phenyl; phenyl monosubstituted with lower alkyl, nitro, halogenated methyl, halogen, and lower alkoxy; and trans-phenylcyclopropyl in which the phenyl group may be substituted with lower alkyl and halogen.

Detailed Description

The compounds of the invention are carboxamide derivatives of 2-oxo-furan. As used herein, "halogen" refers to chlorine, fluorine, bromine and iodine (preferably chlorine) and the terms "lower alkyl" and "lower alkoxy" refer to straight and branched chain alkylene groups having 1 to 4 carbons.

The 2-trans-phenylcyclopropyl derivatives of the invention can be prepared as illustrated in the following diagram which involves a base-catalyzed cyclocondensation of ethyl 4-chloroacetoacetate I with an appropriate trans-phenylcyclopropyl isocyanate II, in which $R^3$ represents lower alkyl or halogen, to provide the esters III. Alkaline hydrolysis of esters III gives the corresponding free acids IV which in turn can be treated with anilines V in the presence of triethylamine and bis(2-oxo-3-oxazolidinyl)phosphinic chloride (BOP-Cl) to provide the lactones VI by a rearrangement.

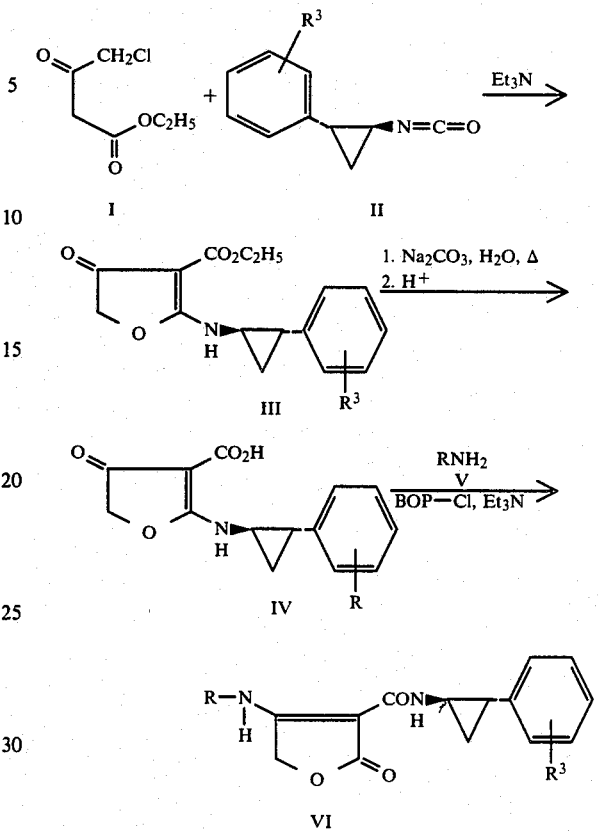

The N-(substituted phenyl)-2,5-dihydro-2-oxo-4-[(substituted phenyl)amino]-3-furancarboxamide derivatives of the invention are similarly obtained by a rearrangement resulting from the reaction of 2-(phenylamino)-4,5-dihydro-4-oxo-3-furancarboxylic acids with an appropriate aniline compound in the presence of bis-(2-oxo-3-oxazolidinyl)phosphinic chloride (BOP-Cl).

The invention is further illustrated by, but is not intended to be limited to, the following examples which describe the preparation of a number of compounds of the invention.

EXAMPLE 1

Preparation of N-(2-trans-Phenylcyclopropyl)-2,5-dihydro-2-oxo-4-[(m-methylphenyl)amino]-3-furancarboxamide Under nitrogen atmosphere, triethylamine (2.22 grams, 22 mmol) was added dropwise to a solution of 4,5-dihydro-4-oxo-2-[(2-trans-phenylcyclopropyl)amino]-3-furancarboxylic acid (2.85 grams, 10 mmol) in 22 ml methylene chloride, at 0° C. (ice/water bath). Then, m-toluidine (1.24 grams, 11.57 mmol) was added, the reaction mixture was allowed to warm to 10° C., and bis-(2-oxo-3-oxazolidinyl)phosphinic chloride (BOP-Cl) (2.8 grams, 11 mmol) was added in one portion. The mixture was stirred at 10° C. for 15 min, and at 20° C. for an additional 2.5 hours. Water (25 ml) was added and the mixture was acidified to pH 1 with 4N hydrochloric acid. The two layers were separated and the aqueous phase was extracted with methylene chloride. The combined extracts were washed sequentially with water and 5% aqueous sodium bicarbonate. After removal of the solvent and recrystallization of the resulting residue from ethanol, 3.33 grams of the crystalline lactone melting at 136°–137° C. were obtained.

EXAMPLES 2–5

The following compounds were prepared by procedures similar to that of Example 1 using the appropriate aniline derivative in place of m-toluidine: N-(2-trans-phenylcyclopropyl)-2,5-dihydro-2-oxo-4-[(m-nitrophenyl)amino]-3-furancarboxamide (R=$C_6H_4NO_2$—m, mp 188°–190° C.); N-(2-trans-phenylcyclopropyl)-2,5-dihydro-2-oxo-4-[(p-chlorophenyl)amino]-3-furancarboxamide R=$C_6H_4Cl$—p, mp 107°–109° C.); N-(2-trans-phenylcyclopropyl)-2,5-dihydro-2-oxo-4-[(3,5-dimethoxyphenyl)amino]-3-furancarboxamide (R=$C_6H_4(CH_3O)_2$—3,5, mp 131°–133° C.); and N-(2-trans-phenylcyclopropyl)-2,5-dihydro-2-oxo-4-[(m-trifluoromethylphenyl)amino]-3-furancarboxamide (R=$C_6H_6CF_3$—m, mp 131°–133° C.

EXAMPLE 6

Preparation of N-Phenyl-2,5-dihydro-2-oxo-4-[N-(p-chlorophenyl)amino]-3-furancarboxamide Under nitrogen atmosphere, 8.5 ml of triethylamine was added dropwise over a period of 40 min to a solution of 2-anilino-4-oxo-3-furoic acid (13.37 grams, 0.061 mol) in 110 ml methylene chloride at 0° C. Then BOP-Cl was added in one portion and the mixture was stirred at 0°–5° C. for 45 min. A solution of p-chloroaniline (7.8 grams, 61 mmol) in 50 ml methylene chloride was added rapidly over 10 min followed by the dropwise addition (1.5 hours) of a solution of triethylamine (8.5 ml) in 10 ml methylene chloride. The reaction mixture was stirred at 0°–5° C. for 30 min and at room temperature for 20 hours. After cooling, 150 ml of water were added and the reaction mixture was acidified with 4N hydrochloric acid (pH 1), and then extracted with methylene chloride. The organic extract was washed sequentially with water, 5% aqueous solution of sodium bicarbonate, and water. The washed extract was dried over sodium sulfate and the solvent evaporated under reduced pressure. The crude product was recrystallized from toluene. Yield: 9.2 gram, mp 209°–210° C. (R=$C_6H_4Cl$—p).

EXAMPLE 7

Preparation of N-Phenyl-2,5-dihydro-2-oxo-[N-(p-methylphenyl)amino]-3-furancarboxamide Under nitrogen atmosphere, BOP-Cl (5.09 grams, 0.02 mol) was added in one portion to a well-stirred solution of 2-anilino-4-oxo-3-furoic acid (4.38 grams, 0.02 mol) and triethylamine (2.8 ml, 20 mmol) in 34 ml methylene chloride, at 0° C. The reaction mixture was stirred at 0° C. for 45 min after which time 2.35 grams (0.022 mol) of p-toluidine in 17 ml methylene chloride were added over a period of 15 min. followed by the dropwise addition of triethylamine (2.8 ml, 20 mmol). The reaction mixture was stirred at 5°–10° C. for 30 min and at room temperature for 2 hours, poured into ice-water, acidified with 2N hydrochloric acid (pH 1), and then extracted with methylene chloride. The organic extract was washed with 5% aqueous sodium bicarbonate solution, dried over sodium sulfate, and the solvent evaporated under reduced pressure leaving the crude product which was recrystallized from ethanol. Yield: 3.37 grams, mp 181°–183° C. (R=$C_6H_4CH_3$—p).

EXAMPLE 8

Preparation of N-Phenyl-2,5-dihydro-2-oxo-4-[(N-phenyl-N-methyl)amino]-3-furancarboxamide Under nitrogen atmosphere, a solution of triethylamine (4.48 ml, 0.032 mol) in 15 ml methylene chloride was added dropwise to a solution of 2-anilino-4-oxo-3-furoic acid (7.01 grams, 0.032 mol) in 43 ml methylene chloride, at 0°–5° C. Then BOP-Cl (8.17 g, 0.032 mol) was added in one portion and the reaction mixture was stirred for 45 min. A solution of N-methylaniline (3.77 grams, 0.035 mol) in 28 ml methylene chloride was added rapidly at 0°–5° C. followed by a dropwise addition of triethylamine (4.48 ml, 0.032 mol) in 15 ml methylene chloride. The reaction mixture was stirred for 30 min at 0°–5° C. and at room temperature for 16 hours, poured into 125 ml ice-water and acidified with 4N hydrochloric acid (pH 1). Following extraction with methylene chloride, the organic extract was washed sequentially with water and 3% aqueous solution of sodium bicarbonate, dried over sodium sulfate, and the solvent evaporated under reduced pressure. The crude product was recrystallized from ethanol. Yield: 2.65 grams, mp 156°–158° C. ($R^1$=$CH_3$).

EXAMPLE 9

Preparation of N-Phenyl-2,5-dihydro-2-oxo-4-phenylamino-3-furancarboxamide

The title derivative was obtained by a procedure similar to that described in Example 8 starting with 2-anilino-4-oxo-3-furoic acid (7.01 grams, 0.032 mol), triethylamine (8.98 ml, 0.064 mol), BOP-Cl (8.15 grams, 0.032 mol) and aniline (2.95 ml, 0.32 mol) dissolved in 100 ml methylene chloride. Yield: 7.37 g, mp 175°–176° C.

EXAMPLE 10

Preparation of N-(m-Nitrophenyl)-2,5-dihydro-2-oxo-4-phenylamino-3-furancarboxamide The title derivative was prepared by a procedure similar to that described in Example 8 starting with 2-[(m-nitrophenyl)amino]-4-oxo-3-furoic acid (7.4 grams, 0.028 mol), BOP-Cl (7.13 grams, 0.028 mol) and aniline (2.58 ml, 0.025 mol) dissolved in 90 ml methylene chloride. Yield: 6.71 g, mp 194°–195° C. ($R^2$=$C_6H_4NO_2$—m).

EXAMPLE 11

The following compounds can be prepared by procedures similar to that of Example 8 by the using the appropriate aniline and furoic acid intermediates.
N-(o-methoxyphenyl)-2,5-dihydro-2-oxo-4-[N-(m-trifluoromethylphenyl)amino]-3-furancarboxamide;
N-(m-trifluoromethylphenyl)-2,5-dihydro-2-oxo-4[N-(o-isopropylphenyl)amino]-3-furancarboxamide;
N-(m-methylphenyl)-2,5-dihydro-2-oxo-4-[N-o-nitrophenyl)amino]-3-furancarboxamide;
N-(p-bromophenyl)-2,5-dihydro-2-oxo-4-[N-(p-methoxyphenyl)amino]-3-furancarboxamide;
N-(o-isopropylphenyl)-2,5-dihydro-2-oxo-4-[N-(m-ethoxyphenyl)amino]-3-furancarboxamide; and
N-phenyl-2,5-dihydro-2-oxo-4[N-(p-butylphenyl)amino]-3-furancarboxamide.

Compounds of the invention have shown antiallergic activity, for example, in the rat dermal vascular permeability assay system and in the rat active anaphylaxis model at a dosage of 100 mg/Kg of body weight. In the rat dermal vascular permeability test, groups of ten male rats are intraperitoneally administered either the test compound or the positive reference standard cyproheptadine (1 mg/kg, ip) one hour prior to an intravenous injection of 1 ml of a 0.5% solution of Evan's blue dye into naive animals. Ten minutes later, the animals are challenged by intradermally injecting 0.1 ml of a solution of either serotonin (1 ug/ml), histamine (20 ug/ml) or bradykinin (10 ug/ml) into separate sites on the back. Five minutes following challenge the animals are killed, the skin retracted, and the mean diameter of the blue wheal and flare reactions determined. The percent inhibition of the wheal reaction is calculated as the difference in diameter between the saline control and drug treated groups divided by the control diameter times 100. Statistical analysis of the data is done using the poolt program. According to this test, the compound of Example 3 produced the most potent antiallergy activity of the compounds tested showing over 90% inhibition with respect to serotonin, histamine and bradykinin.

We claim:

1. A Compound of the formula:

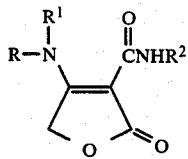

Where R is selected from phenyl and phenyl mono or disubstituted with lower alkyl, nitro, halogenated methyl, halogen, lower alkoxy and combinations thereof;

Where $R^1$ is selected from hydrogen and lower alkyl; and

Where $R^2$ is selected from phenyl; phenyl monosubstituted with lower alkyl, nitro, halogenated methyl, halogen and lower alkoxy; and trans-phenylcyclopropyl in which the phenyl group may be substituted with lower alkyl and halogen.

2. A compound according to claim 1 wherein $R^2$ is trans-phenylcyclopropyl.

3. The compound of claim 2 wherein the compound is N-(2-trans-phenylcyclopropyl)-2,5-dihydro-2-oxo-4-[(m-methylphenyl)amino]-3-furancarboxamide.

4. The compound of claim 2 wherein the compound is N-(2-trans-phenylcyclopropyl)-2,5-dihydro-2-oxo-4-[(m-nitrophenyl)amino]-3-furancarboxamide.

5. The compound of claim 2 wherein the compound is N-(2-trans-phenylcyclopropyl)-2,5-dihydro-2-oxo-4-[(p-chlorophenyl)amino]-3-furancarboxamide.

6. The compound of claim 2 wherein the compound is N-(2-trans-phenylcyclopropyl)-2,5-dihydro-2-oxo-4-[(3,5-dimethoxyphenyl)amino]-3-furancarboxamide.

7. The compound of claim 2 wherein the compound is N-(2-trans-phenylcyclopropyl)-2,5-dihydro-2-oxo-4-[(m-trifluoromethylphenyl)amino]-3-furancarboxamide.

8. The compound of claim 1 wherein the compound is N-phenyl-2,5-dihydro-2-oxo-4-[N-(p-chlorophenyl)amino]-3-furancarboxamide.

9. The compound of claim 1 wherein the compound is N-phenyl-2,5-dihydro-2-oxo-4-[N-(p-methylphenyl)amino]-3-furancarboxamide.

10. The compound of claim 1 wherein the compound is N-phenyl-2,5-dihydro-2-oxo-4-[(N-phenyl-N-methyl)amino]-3-furancarboxamide.

11. The compound of claim 1 wherein the compound is N-phenyl-2,5-dihydro-2-oxo-4-phenylamino-3-furancarboxamide.

12. The compound of claim 1 wherein the compound is N-(m-nitrophenyl)-2,5-dihydro-2-oxo-4-phenylamino-3-furancarboxamide.

* * * * *